United States Patent [19]

Hsu et al.

[11] Patent Number: 4,482,756
[45] Date of Patent: Nov. 13, 1984

[54] PRODUCTION OF HYDROQUINONES

[75] Inventors: Chao-Yang Hsu, Media; James E. Lyons, Wallingford, both of Pa.

[73] Assignee: Sun Tech, Inc., Philadelphia, Pa.

[21] Appl. No.: 511,111

[22] Filed: Jul. 5, 1983

Related U.S. Application Data

[63] Continuation-in-part of Ser. No. 372,874, Apr. 29, 1982, abandoned.

[51] Int. Cl.$^3$ .................... C07C 39/08; C07C 37/00
[52] U.S. Cl. .................................... 568/772; 568/771
[58] Field of Search .............................. 568/772, 771

[56] References Cited

U.S. PATENT DOCUMENTS

| 1,495,521 | 1/1950 | Hannion et al. | 568/772 |
| 3,213,114 | 10/1965 | Braxton et al. | 568/772 |
| 3,842,130 | 10/1974 | Kawaguchi et al. | 568/772 |
| 3,927,045 | 12/1975 | Michelet et al. | 568/772 |
| 3,954,891 | 5/1976 | Orth et al. | 568/772 |
| 4,208,339 | 6/1980 | Costanini et al. | 568/772 |
| 4,235,790 | 11/1980 | Müller et al. | 568/772 |
| 4,250,336 | 2/1981 | Müller et al. | 568/772 |

FOREIGN PATENT DOCUMENTS

| 2160599 | 7/1973 | Fed. Rep. of Germany | 568/772 |
| 2432230 | 1/1976 | Fed. Rep. of Germany | 568/772 |
| 2802863 | 7/1979 | Fed. Rep. of Germany | 568/772 |
| 50-55694 | 3/1975 | Japan | 568/772 |
| 786106 | 11/1957 | United Kingdom | 568/772 |

OTHER PUBLICATIONS

Naile et al., "Comptes Rend", Ac. Sc. vol. 144, pp. 457–458, (1908).
Sabstier et al., "Comptes Rend", Ac. As., vol. 172, pp. 733–736, (1921).
Cornubert et al., "Comptes Rend", Ac. Sc., vol. 229, pp. 460–462, (1949).
Popova et al., "Chem. Abst.", vol. 61, p. 275f, (1959).
Calvin, "J. Amer. Chem. Soc.", vol. 61, pp. 2230–2234, (1939).
Berkman et al., "Catalysis", p. 760, Reinhold Pub., 1940.

Primary Examiner—Werren B. Lone
Attorney, Agent, or Firm—J. Edward Hess; Donald R. Johnson; Stanford M. Back

[57] ABSTRACT

A process for making a hydroquinone from phenol or substituted phenol wherein the phenol is oxidized in the presence of a copper catalyst to a p-benzoquinone compound and the p-benzoquinone compound is directly hydrogenated without additional catalyst to the corresponding hydroquinone.

19 Claims, No Drawings

PRODUCTION OF HYDROQUINONES

This application is a continuation-in-part of Ser. No. 372,874, filed Apr. 29, 1982, now abandoned.

BACKGROUND OF THE INVENTION

It is known to oxidize phenol to p-benzoquinone in the presence of copper catalysts; see for example U.S. Pat. No. 3,987,068. Improvements to these copper catalyzed oxidations of phenol to p-benzoquinone have been disclosed and claimed in U.S. Ser. No. 284,893, filed July 20, 1981, and U.S. Ser. No. 339,965, filed Jan. 18, 1982, which disclosures are hereby incorporated by reference.

Heretofore, p-benzoquinone has been converted to hydroquinone by use of various catalysts. Thus, for example, Sabatier passed quinone vapors mixed with hydrogen over a reduced copper catalyst (e.g., a heterogeneous vapor phase system) to obtain hydroquinone (Comptes rendus Ac. Sc. vol. 146, p. 457, 1908 and vol. 172 p. 733, 1921), but in this process the catalyst has a very limited life. R. Cornubert and J. Phelisse, Compt. Rend. 229, 460 (1949) disclose use of Raney nickel to convert quinone to hydroquinone. U.S. Pat. No. 2,495,521 discloses nickel, cobalt, or copper catalyzed heterogeneous vapor phase hydrogenation of benzoquinone in the presence of steam. Popova et al., Chem. Abs. 53,275 (1959) disclose hydrogenation of benzoquinone with nickel, platinum and palladium—calcium carbonate. M. Calvin, J. Am. Chem. Soc., 61, 2230 (1939) discloses use of a copper-quinoline complex derived from cuprous acetate to promote hydrogenation of purified quinone, but this process is limited in that, at most, only one-half mole of hydrogen is taken up per mole of the Copper I—quinoline complex and thus the hydrogenation is very inefficient and perhaps not catalytic. Also of interest is the disclosure of Yananaka et al., Bull. Inst. Phys. Chem. Research (Tokyo) 14, 31 1935 which reduces quinones to oxy compounds with copper and Al$_2$O$_3$-promoted nickel.

BRIEF STATEMENT OF THE INVENTION

It has now been found that a good yield of hydroquinone and substituted hydroquinones is readily obtained when the p-benzoquinone compound formed in a reaction mass obtained by oxidation of a phenol with a copper catalyst is hydrogenated directly, i.e., without isolation, and without any additional catalyst. It is quite obvious that such a "one-pot" process provides a highly efficient means to obtain hydroquinone and substituted hydroquinones which are commercial chemicals much used in the photographic industry and as inhibitors used in the stabilization of rubber compounds.

DETAILED DESCRIPTION OF THE INVENTION

Phenols and substituted phenols used in this invention are converted into substituted hydroquinones in accord with the process of the invention as illustrated by the following equation:

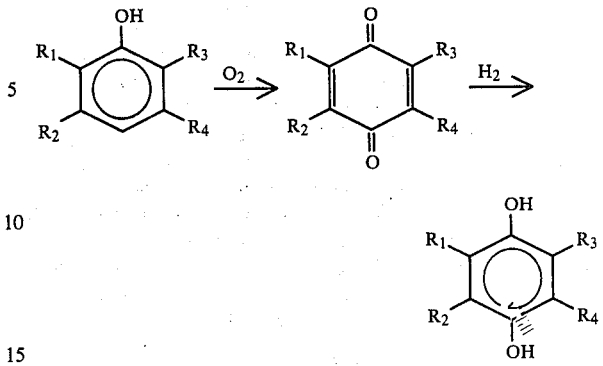

where the ring substitutents: R$_1$, R$_2$, R$_3$ and R$_4$ may be the same or different radicals selected from the group consisting of hydrogen, halo, cyano, alkyl and alkoxy having from 1 to 12 carbon atoms, phenyl, naphthyl, phenylalkyl and alkylphenyl radicals having from 7 to 16 carbon atoms and R$_1$ and R$_2$ or R$_3$ and R$_4$ may be joined to form an aliphatic, aryl or hetero ring. When the R groups as defined above are other than hydrogen, R$_1$, R$_2$, R$_3$ and R$_4$ may be in any position except the para position. Specific R groups are exemplified by chloro, cyano, methyl, ethyl, propyl, butyl, isobutyl, tert-butyl, pentyl, phenyl, p-tolyl, p-anisyl, methoxy, t-butoxy, phenoxy, p-methylphenoxy, and the like. Preferred phenols useful in the process are phenol, o-chlorophenol, o-cresol, m-cresol, 2,5- and 2,6-di-t-butylphenol, 2-t-butylphenol, 2,6-dimethylphenol, and 1-naphthol. When R$_1$ and R$_2$ or R$_3$ and R$_4$ are joined the resulting 1,4-hydroquinone will be those derived from naphthalene, quinoline, isoquinoline, chroman (dihydrobenzopyran), indole and the like.

The oxidation of phenol to p-benzoquinone with a copper catalyst is, as indicated, well known in the art and any of such processes may be used in the first step of this invention. Preferably a process such as that disclosed in U.S. Pat. No. 3,987,068 will be used, which disclosure is hereby incorporated by reference. Most preferably, the hydrogenation step of this invention will be used with the processes disclosed in (a) Ser. No. 284,893, filed July 20, 1981, where a divalent copper catalyst promoted with an alkali metal hydroxide is used (molar ratio of base to copper being no greater than about 2.0) and may also be further enhanced with water in an amount less than about 10% by volume of the reaction solution, and (b) Ser. No. 339,965, filed Jan. 18, 1982, where a monovalent copper catalyst promoted with water is used (preferably 1 to 4 moles of water per mole of phenol).

The hydrogenation step in the process will be carried out in a homogeneous, liquid phase system simply by first removing oxygen from the system and then pressuring in hydrogen to a pressure of about 500 to about 5000 psig (preferably about 1000 to about 3000) and effecting the hydrogenation at a temperature between about 100° and about 200° C., preferably from about 125° to about 175° C.

In order to further exemplify the process the following examples are given:

EXAMPLE 1

500 mmole of phenol is oxidized in 350 ml of acetonitrile containing 35 mmole of CuCl$_2$. An oxygen containing gas (39% O$_2$, 61% N$_2$) is continuously sparged through the mixture at 65° C. and 750 psi at 500 ml/hr. After four hours the reaction mixture contains four mmole of phenol, 263 mmole of benzoquinone and six mmole of p-chlorophenol (99% conv., 53% selectivity). The oxygen is flushed from the system and hydrogen gas is admitted to a pressure of 3,000 psi. The mixture is heated for fifteen hours at 175° C. to give 135 mmoles of hydroquinone, 2 mmoles unreacted p-benzoquinone, 17 mmoles catechol, 6 mmoles of p-chlorophenol, 17 mmoles of phenol and a large amount of quinhydrone (a 1:1 complex of hydroquinone and p-benzoquinone). Yield calculations are difficult because of the low accuracy of the quinhydrone analysis, but a yield of up to about 71% is believed to be achieved.

EXAMPLE 2

In an experiment similar to Example 1 except that the $CuCl_2$ catalyst is promoted with LiOH (one mole per mole of $CuCl_2$) selectivity to p-benzoquinone is about 70% at 99% conversion. The reaction mixture is hydrogenated by pressurizing 2000 psi of hydrogen on it at 175° C. to give a yield of hydroquinone about the same as in Example 1.

EXAMPLE 3

Similar results are obtained when the process of Example 1 is carried out with a CuCl catalyst promoted with 500 mmole of water.

EXAMPLE 4

In an experiment similar to Example 1 except that o-cresol is used in place of phenol, a good yield of methyl-p-benzoquinone is obtained which is hydrogenated to 1,4-dihydroxy-2-methylbenzene.

EXAMPLE 5

Following the detail of Example 2 except that m-cresol is used in place of phenol, 1,4-dihydroxy-2-methylbenzene is obtained in satisfactory yield.

EXAMPLE 6

When Example 1 is repeated except that 2,6-dimethylphenol is used in place of phenol, a good yield of 1,4-dihydroxy-2,6-dimethyl-benzene is obtained.

EXAMPLE 7

In an experiment similar to Example 2 except that 2,6-di-t-butylphenol is used in place of phenol, 2,6-di-t-butyl-1,4-dihydroxybenzene is obtained in good yield.

EXAMPLE 8

When Example 1 is repeated except that o-t-butylphenol is used in place of phenol tert-butylhydroquinone is obtained in a quite satisfactory yield.

EXAMPLE 9

Following the details of Example 1 except that 2,5-di-tert-butylphenol is used in place of phenol, 2,5-di-tert-butylhydroquinone is obtained in good yield.

We claim:

1. A process for making a hydroquinone compound from phenol or a substituted phenol in a homogeneous liquid phase reaction, comprising (a) contacting said phenol or substituted phenol with oxygen at elevated pressure in the presence of a copper catalyst to form the corresponding p-benzoquinone, (b) removing unreacted oxygen, and (c) in the same reaction mass without additional catalyst or separation of the p-benzoquinone compound, contacting the p-benzoquinone compound with hydrogen at elevated temperature and pressure to form said hydroquinone compound.

2. The process of claim 1 wherein the copper catalyst used in step (a) is divalent and is promoted with an alkali-metal compound.

3. The process of claim 1 wherein the copper catalyst used in step (a) is monovalent and is promoted with water.

4. The process of claim 1 wherein step (c) is effected at a hydrogen pressure of about 500 to about 5000 psig and at a temperature of about 100° C. to about 200° C.

5. The process of claim 1 wherein the process is effected in acetonitrile.

6. A process for making hydroquinone from phenol in a homogeneous liquid phase reaction, comprising (a) contacting phenol with oxygen at elevated pressure in the presence of a copper catalyst to form p-benzoquinone, (b) removing unreacted oxygen, and (c) in the same reaction mass without additional catalyst or separation of the p-benzoquinone, contacting the p-benzoquinone with hydrogen at elevated temperature and pressure to form hydroquinone.

7. The process of claim 6 wherein the copper catalyst used in step (a) is divalent and is promoted with an alkali-metal compound.

8. The process of claim 6 wherein the copper catalyst used in step (a) is monovalent and is promoted with water.

9. The process of claim 6 wherein step (c) is effected at a hydrogen pressure of about 500 to about 5000 psig and at a temperature of about 100° C. to about 200° C.

10. The process of claim 6 wherein the process is effected in acetonitrile.

11. A process for making a hydroquinone from substituted phenol in a homogeneous liquid phase reaction, comprising (a) contacting phenol with oxygen at elevated pressure in the presence of a monovalent copper catalyst promoted with water or a divalent copper catalyst promoted with an alkali metal compound to form the corresponding p-benzoquinone compound, (b) removing unreacted oxygen, and (c) in the same reaction mass without additional catalyst or separation of the p-benzoquinone, contacting the p-benzoquinone with hydrogen at a temperature of from about 100° C. to about 200° C. and at a pressure of from about 500 to about 5000 psig to form said hydroquinone compound.

12. The process of claim 11 wherein the process is effected in acetonitrile.

13. The process of claim 12 wherein the phenol is an alkylated phenol.

14. The process of claim 13 wherein the alkylated phenol is o-cresol.

15. The process of claim 13 wherein the alkylated phenol is m-cresol.

16. The process of claim 13 wherein the alkylated phenol is 2,6-dimethylphenol.

17. The process of claim 13 wherein the alkylated phenol is 2,6-di-t-butylphenol.

18. The process of claim 13 wherein the alkylated phenol is o-t-butylphenol.

19. The process of claim 13 wherein the alkylated phenol is 2,5-di-t-butylphenol.

* * * * *